United States Patent [19]

Masaki

[11] Patent Number: 5,484,386

[45] Date of Patent: Jan. 16, 1996

[54] HAMMER-LIKE TOOL FOR RELIEVING STIFFNESS IN THE NECK AND SHOULDER

[75] Inventor: Kazumi Masaki, Osaka, Japan

[73] Assignee: Ken Hayashibara, Okayama, Japan

[21] Appl. No.: 301,816

[22] Filed: Sep. 7, 1994

[30] Foreign Application Priority Data

Sep. 7, 1993 [JP] Japan .................... 5-246157

[51] Int. Cl.⁶ .................................... A61H 23/02
[52] U.S. Cl. ........................ 601/21; 601/15; 601/107
[58] Field of Search ..................... 601/15, 18–21, 601/22, 107–111; 607/2, 46, 150, 154, 156

[56] References Cited

U.S. PATENT DOCUMENTS

| 602,950 | 4/1898 | Lau | 601/20 |
|---|---|---|---|
| 1,955,863 | 4/1934 | Schmidt | 601/18 |
| 4,037,590 | 7/1977 | Dohring | 601/20 |
| 4,095,601 | 6/1978 | Aufranc | 601/20 |
| 4,175,551 | 11/1979 | D'Haenens | 601/15 |

FOREIGN PATENT DOCUMENTS

| 54-58991 | 12/1979 | Japan . |
|---|---|---|
| 56-171040 | 12/1981 | Japan . |
| 60-149644 | 10/1985 | Japan . |
| 61-4629 | 1/1986 | Japan . |
| 1-77743 | 5/1989 | Japan . |
| 2953493 | 4/1993 | Japan . |

OTHER PUBLICATIONS

Shiina, Shinich. Rinsho–Kensa–Koza, vol. 11., 1985. pp. 115–146.
Tadashi Matsuzawa. Proceedings Of The Research University Of Tsukuba School For The Blind. vol. 16., 1983, pp. 75–83.

Primary Examiner—Robert A. Hafer
Assistant Examiner—David J. Kenealy
Attorney, Agent, or Firm—Browdy and Neimark

[57] ABSTRACT

A hammer-like tool for relieving stiffness in the neck and shoulder with an improved therapeutic and prophylactic effect. A cylindrical space is provided in the head of the hammer-like tool, a free-flowing magnet provided in the cylindrical space, an induction coil provided near the periphery of the cylindrical space to surround it, a load coil provided near the face of the hammer-like tool, and a high-frequency oscillator circuit. The load coil generates a high-frequency electromagnetic wave by supplying an electromotive force to the load coil via the high-frequency oscillator when the magnet moves within the cylindrical space.

7 Claims, 5 Drawing Sheets

HAMMER-LIKE TOOL FOR RELIEVING STIFFNESS IN THE NECK AND SHOULDER

BACKGROUND OF THE INVENTION

1. Field of the Invention

The present invention relates to a hammer-like tool for relieving stiffness in the neck and shoulder having a built-in high-frequency oscillator.

2. Description of the Prior Art

Recently, we find many patents and utility models relating to hammer-like tools for relieving stiffness in the neck and shoulder having a built-in magnet for improving their therapeutic and prophylactic effect.

Examples of such are those disclosed in Japanese Patent Laid-Open No. 58,991/79 and Japanese Patent Utility Model Laid-Open Nos. 171,040/81, 149,644/85, 4,629/86 and 77,743/89. Especially, Japanese Patent Utility Model Laid-Open No. 29,534/93 discloses a hammer-like tool for relieving stiffness in the neck and shoulder, having a magnet provided in a cylindrical space within the head, which induces an electromotive force to be imparted to patient's affected parts to improve the desired therapeutic and prophylactic effect, and has an on-off lighting means which is provided in the head and energized by an electromotive force generated by an appropriate combination use of a magnet and a coil.

The Japanese Utility Model Laid-Open No. 29,534/93 is, however, silent on the application of such an electromotive force to preventing and treating patient's affected parts.

SUMMARY OF THE INVENTION

The present invention relates to a hammer-like tool for relieving stiffness in the neck and shoulder having a built-in high-frequency oscillator.

In view of the above prior art, the present inventor energetically studied on a hammer-like tool for relieving stiffness in the neck and shoulder which exerts a more satisfactory therapeutic and prophylactic effect than conventional ones.

The object of the present invention is attained by, in a hammer-like tool for relieving stiffness in the neck and shoulder, constructing (a) a cylindrical space provided in the same direction of its shaking as a head of the hammer-like tool, (b) a or free-floating magnet enclosed in the cylindrical space, (c) an induction coil provided near the periphery of the cylindrical space to surround it, (d) a high-frequency oscillator circuit whose input terminal is connected to the induction coil provided in the head of the hammer-like tool, and (e) a load coil provided near the face of the hammer-like tool, and connecting the load coil to the output terminal of the high-frequency oscillator circuit, whereby a high-frequency electromagnetic wave is generated by an electromotive force induced by the induction coil in a manner that the electromotive force is supplied to the load coil via the high-frequency oscillator circuit as the magnet moves in the cylindrical space.

DESCRIPTION OF THE ACCOMPANYING DRAWINGS

Figure 4:
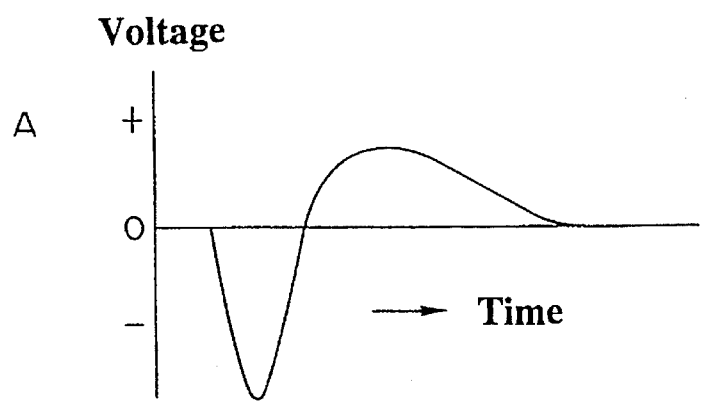
Figure 4:
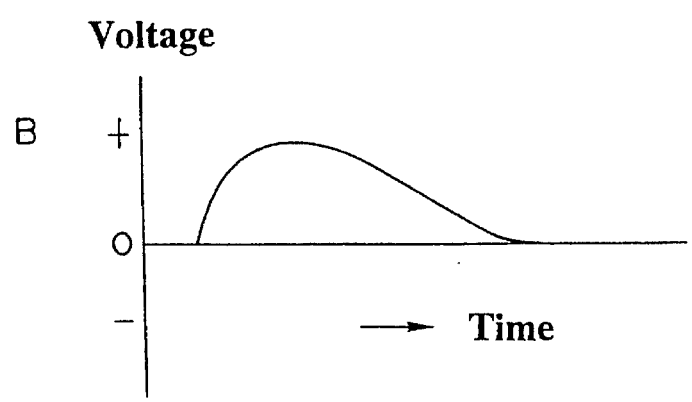
Figure 4:
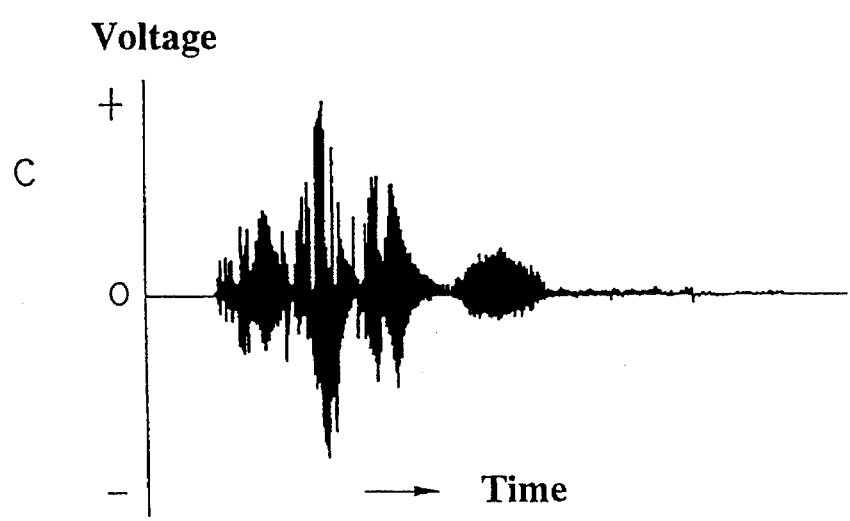

FIG. 4 shows wave changes of voltages observed in patient's affected part and generated therein by the hammer-like tool of the present invention: (A) shows a wave pattern of an electromotive force induced by an induction coil $L_1$, (B) shows a wave pattern of a voltage charged in a capacitor C of a high-frequency oscillator, and (C) shows a wave form of a high-frequency electromagnetic wave generated by a load coil $L_2$.

Figure 5:
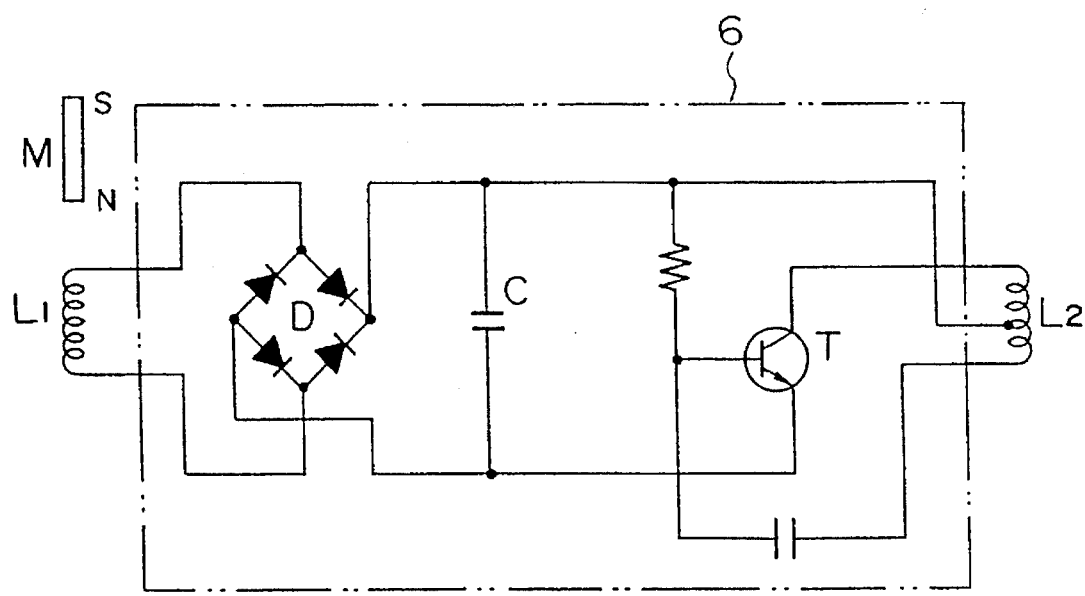

FIG. 5 shows a circuit of an embodiment of the high-frequency oscillator of the present invention.

In the figures, the numeral "1" means the head of the hammer-like tool according to the present invention; "2", handle; "3", grip; "4", cylindrical space; "5", insulator/shock absorber; "6", circuit; "7" case; "$L_1$", induction coil; "$L_2$", load coil; and "M", magnet.

DETAILED DESCRIPTION OF THE INVENTION

The present invention is to treat patient's affected parts with a high-frequency electromagnetic wave and an electromotive force together with a physical function of beating wherein said electromotive force, which is induced by an induction coil provided near the cylindrical space of the head of the present hammer-like tool when a magnet freely moves within the cylindrical space, is supplied to a high-frequency oscillator circuit connected to the output terminal of the induction coil, and said high-frequency electromagnetic wave is generated by a load coil which receives a high-frequency current from the high-frequency oscillator circuit.

Figure 1:
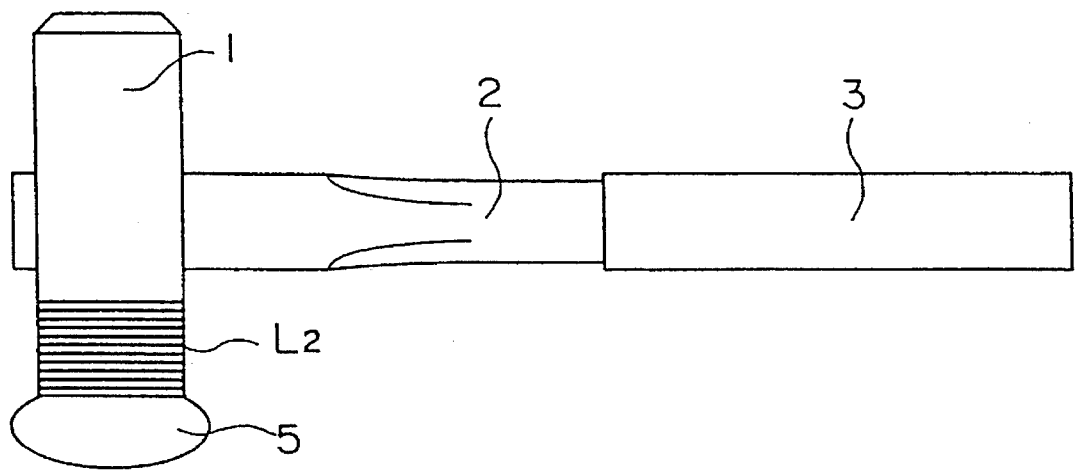
FIG. 1 shows a side elevation view of an embodiment of the hammer-like tool of the present invention.

In order that the present invention may be readily carried into effect, it will now be described with reference to the accompanying drawings, wherein:

FIG. 1 is a side elevation view of the hammer-like tool of the present invention mainly constructed by a head 1 and a handle 2.

Usually, the head 1 is made of a non-magnetic material such as a plastic, wood or rubber, or from their appropriate mixtures, and formed into a cylindrical or square form. The handle 2, which requires a relatively-high mechanical strength, is usually made of those having a relatively-high strength such as a metal, wood, plastic or mixtures thereof. If necessary, the handle 2 can be provided with a grip 3 made of an elastic material such as a plastic or rubber.

A cylindrical space 4 is provided in the head 1, and a magnet M is provided within the cylindrical space 1 in a manner that it moves freely. The cylindrical space 4 is provided to give a relatively-long cylindrical space in the same direction of the head 1 to be swung so as to freely move the magnet M within the cylindrical space 4 when the head 1 is swung.

A shock absorber/insulator 5, which is made of a sponge or rubber, is provided in the face of the head 1 to soften the beat shock of the head 1 against patient's body and that of the magnet M against the face as well as to absorb the sound of beating. As shown in the figure, another shock absorber/insulator 5' can be provided at the inside top of the opposite side of the face of the cylindrical space 4.

An inductor coil $L_1$ is provided to surround the cylindrical space 4. The number of turns of the coil $L_1$ differs dependently on the material used, and those which are suitable for generating a high-frequency electromagnetic wave in the invention are appropriately chosen. If necessary, two or more induction coils $L_1$ can be provided in the present hammer-like tool to meet to its use.

A high-frequency oscillator 6 is provided within the head 1, and the input terminal of the oscillator 6 is connected to the induction coil $L_1$ in order to convert an electromotive force, generated by the induction coil $L_1$, into a high-frequency current.

FIG. 5 is an embodiment of the high-frequency oscillator 6 according to the invention. Now explaining the circuit briefly with reference to its function, the induction coil $L_1$ induces an electromotive force as shown at "A" in FIG. 4 when the magnet M passes through the induction coil $L_1$. The electromotive force is rectified by a rectifier circuit D to charge a capacitor C, and a wave-form as shown as "B" in FIG. 4 results. Usually, the magnet M has a magnetic flux density of about 100–100,000 gauss. The voltage charged in the capacitor C oscillates a transistor T, and a high-frequency current passes through a load coil $L_2$, connected to the output terminal of the high-frequency oscillator 6, to generate a high-frequency electromagnetic wave as shown as "C" in FIG. 4. In this case, an appropriate combination use of the high-frequency oscillator 6, the transistor T and load coil $L_2$ can readily allow the load coil $L_2$ to generate a high-frequency electromagnetic wave ranging from about 100 kHz to 10 MHz. Furthermore, an appropriate high-frequency oscillator circuit is arbitrarily used in the invention as long as it functions similarly as above.

Figure 2:
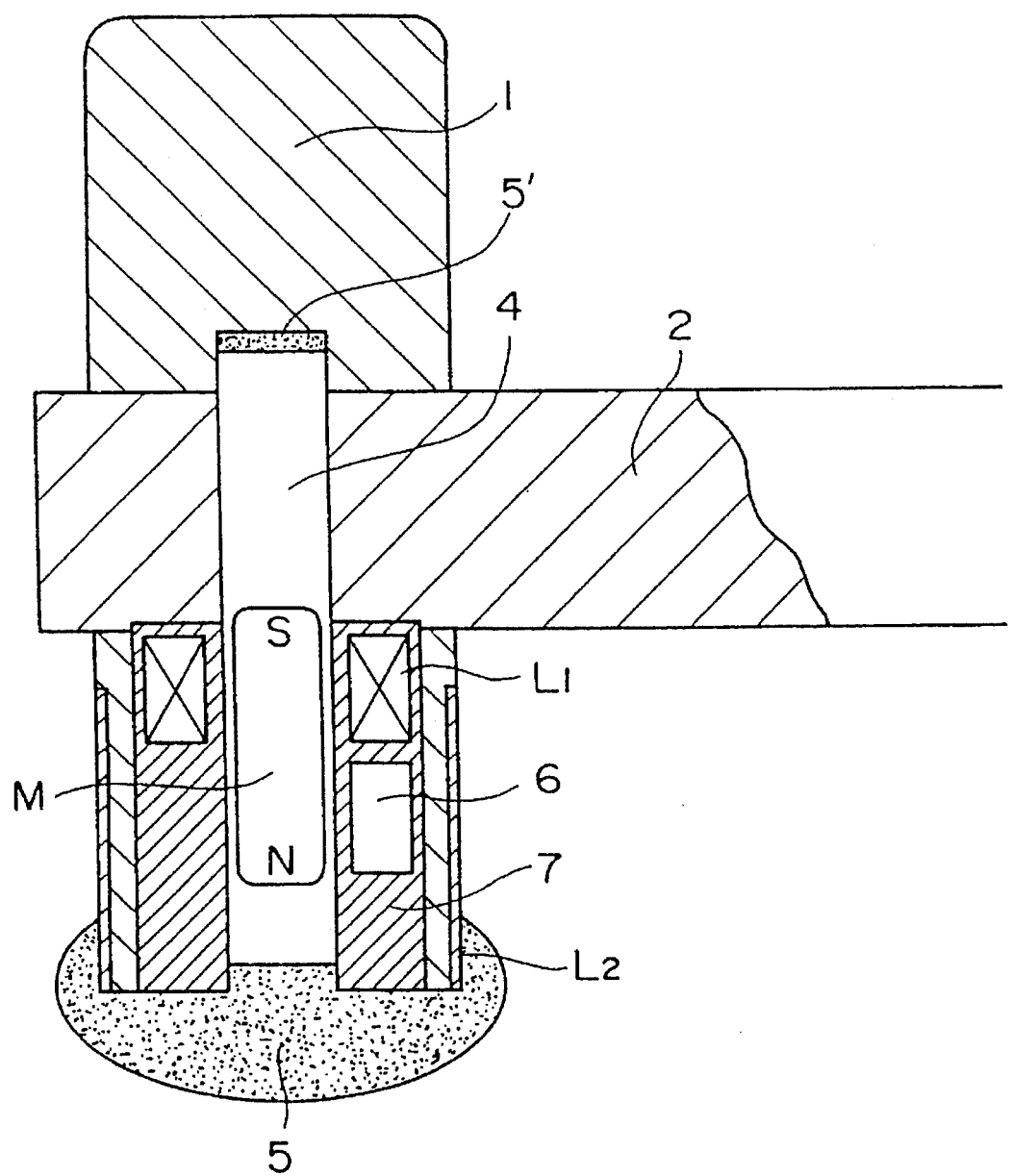
FIG. 2 shows a longitudinal sectional side elevation view of an embodiment of the hammer-like tool of the present invention.
Figure 3:
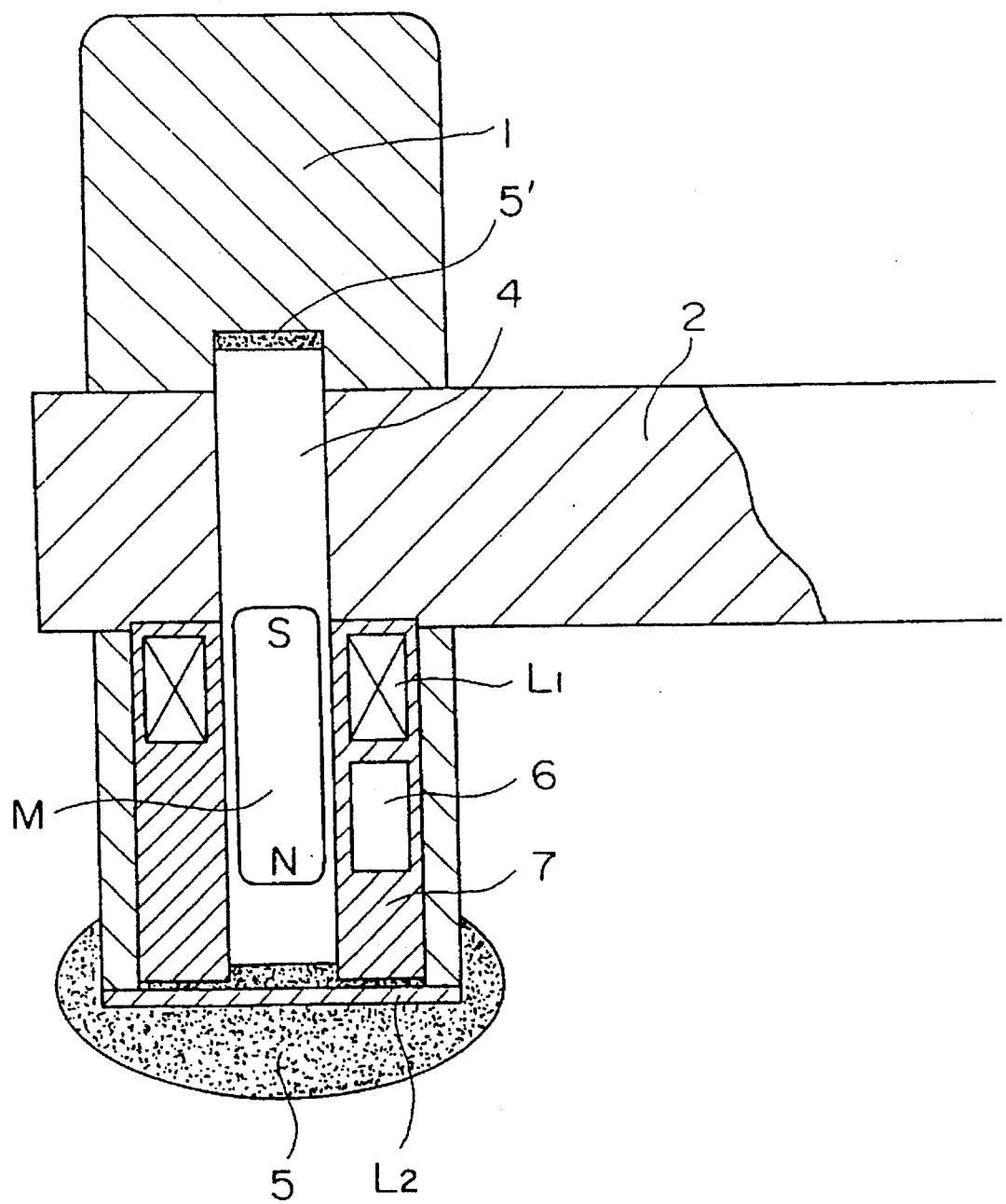
FIG. 3 shows a longitudinal sectional side elevation view of another embodiment of the hammer-like tool of the present invention.

The load coil $L_2$ is provided near at the head 1. As shown in FIGS. 1 and 2, the load coil $L_2$ can be arranged spirally along with the outer surface near at the head 1, or arranged horizontally against the face of the head 1 as shown in FIG. 3. The number of turns of the load coil $L_2$ is appropriately chosen so as to sufficiently generate a high-frequency electromagnetic wave requisite for attaining the object of the invention.

In the figures, the numeral 7 means an appropriate cylindrical case which is provided for the sake of readily housing the induction coil $L_1$ and the high-frequency oscillator 6 and installing them in the head 1.

As described above, since the hammer-like tool according to the present invention installs the load coil $L_2$ near at the face of the head 1, both a magnetic force generated by the magnet M and a high-frequency electromagnetic wave generated by the load coil $L_2$ at the moment the head 1 locates to the nearest of a patient's body pass through the patient's affected parts.

Experiment

Effect of the present hammer-like tool on relieving stiffness in the neck and shoulder Volunteers who were claiming stiffness in the neck and/or shoulder treated themselves by beating their dorsal cucullaris with a hammer-like tool installed with a high-frequency oscillator circuit as shown in FIG. 5, and measured their micro-vibrations (hereinafter abbreviated as "MV") and plethysmograms (hereinafter abbreviated as "PTG") in accordance with the methods as described by Tadashi MATSUZAWA in *Proceedings of the Research of University of Tsukuba School for the Blind*, Vol.16, pp.75–83 (1983) and by Shinich SHIINA in *Rinsho-Kensa-Koza*, Vol.11, pp.115–146 (1985). In this experiment a transistor T and a load coil $L_2$, installed in the high-frequency oscillator circuit as shown in FIG. 5, were appropriately arranged to allow the load coil $L_2$ to generate a high-frequency electromagnetic wave of 2 MHz.

The MV was detected with a voltage element, and micro-vibrations of ballistic components, which were generated in muscular fibers and accompanied by heartbeats in vivo, were converted into electric signals for recording. Muscular tension induced by stiffness in the neck and/or shoulder was detected as a peak of a high-frequency vibration, while a peak of a low-frequency vibration was detected when the stiffness in the neck and/or shoulder was removed or relieved. Therefore, the efficacy of the treatment can be evaluated by observing whether a peak of a low-frequency vibration is formed or whether the augmentation thereof is reflected in the MV pattern.

The PTG was detected by monitoring a blood rate as a pressure change of a blood vessel, and the volume change was expressed as a pulse level. It is understood that the increment of the blood rate in the affected parts and the pulse level represents the efficacy of the present hammer-like tool on the stiff in the neck and/or shoulder.

Now explaining the experiment in more detail, 10 male volunteers, 40–45-year-old, who were claiming a stiffness in the neck and/or shoulder, were with pickups with surgical tapes on their dorsal cucullaris to detect their MV and PTG, and allowed to relax and sit on a sofa. Five minutes later, the volunteers beat their shoulders with the present hammer-like tool, installed with a high-frequency oscillator circuit as shown in FIG. 5, at a comfortable beat-strength. The beating procedure was performed for 3 minutes in such a manner that they were allowed to successively and repeatedly beat themselves on their shoulders for 10 seconds at a constant beating rate of 15 times per 10 seconds, cease the beating for 5 seconds, and beat their shoulders at the same beating rate for 10 seconds.

During 15 minutes after completion of the beating procedure, the MV and PTG of the treated affected-parts of the volunteers were recorded. The MV and PTG were measured by using "MT-3T", a MV pickup commercialized by Nippon Denki Sanei Kabushiki-Kaisha, Tokyo, Japan; "POLYGRAPH MODEL 97A", a PTG pickup commercialized by Nippon Denki Sanei Kabushiki-Kaisha, Tokyo, Japan; "XR-710", a data recorder commercialized by Teac Corporation, Tokyo, Japan; and "MODEL 7T18A", a signal processor commercialized by Nippon Denki Sanei Kabushiki-Kaisha, Tokyo, Japan.

In this experiment, the volunteers were measured on their MV and PTG before and 0, 3, 5, 7, 9, 11, 13 and 15 minutes after the treatment with the present hammer-like tool, and the data were analyzed for judging the efficacy.

As a result, the volunteers before the treatment showed MV patterns having a considerably-high peak in a region of a relatively-high frequency of about 7 Hz, a specific peak detected in the muscular system in a state of tension, while after the treatment their MV patterns altered to show a considerably-high peak of about 4 Hz, a specific peak detected in the muscular system in a state of relaxation. This indicates that the hammer-like tool according to the present invention effectively relaxed stiff muscles in the neck and shoulder.

As regards the PTG of the volunteers, when the value before the treatment was considered as 100%, the average value just after the treatment was about 150%. The average value 3 minutes after the treatment was about 200%. The average value 5 minutes after the treatment was about 210%. The average value 7–15 minutes after the treatment was in the range of about 220–250%. These revealed that the hammer-like tool according to the present invention effectively improved the blood circulation in the volunteers' affected parts.

About one-hour monitoring of the dynamics of the blood circulation after the treatment revealed that the blood circulation once improved retained a relatively-high level through over the period.

As a control, the volunteers were similarly as in the above allowed to beat themselves with a hammer-like tool in which the connection of the induction coil $L_1$ and the rectifier circuit in the high-frequency oscillator circuit 6 was short-circuited so as not to generate a high-frequency electromagnetic wave by a load coil $L_2$. The MV pattern and PTG of the volunteers as a control were absolutely inferior to those of the volunteers who had been treated with the present hammer-like tool.

As is obvious from the above, the hammer-like tool according to the present invention exerts a satisfactory efficacy on patient's affected parts by treating them with the hammer-like tool to give a synergistic effect of a physical beating, an electromotive force induced by a magnet, and a high-frequency electromagnetic wave generated by a load coil. The present hammer-like tool more effectively accelerates the metabolism of patient's affected parts than other conventional tools.

Thus, the present hammer-like tool acts on stiff in the neck, shoulder, back and limbs as well as lumbago and cephalic congestion, improves their symptoms, relieves pains accompanied by the symptoms, and satisfactorily prevents the symptoms.

The present hammer-like tool is also useful as a means to treat and prevent a variety of stiffness.

While there has been described what is at present considered to be the preferred embodiments of the invention, it will be understood the various modifications may be made therein, and it is intended to cover in the appended claims all such modifications as fall within the true spirits and scope of the invention.

I claim:

1. A hammer-like tool for relieving stiffness in the neck and shoulder, which comprises:
   (a) an elongated cylindrical housing provided as a head of said hammer-like tool;
   (b) a free-floating magnet having a magnetic flux of about 100–100,000 gauss, enclosed in said cylindrical housing;
   (c) an induction coil provided near the periphery of said cylindrical housing to surround it;
   (d) a high-frequency oscillator circuit having an input terminal connected to said induction coil and being provided in the head of said hammer-like tool, said circuit generating a high-frequency current; and
   (e) a load coil provided near the face of said hammer-like tool and connected to the output terminal of said high-frequency oscillator circuit, said load coil generating a high-frequency electromagnetic wave in the range of about 100 KHz to 10 MHz.

2. The hammer-like tool in accordance with claim 1, wherein said cylindrical housing is made of a non-magnetic material.

3. The hammer-like tool in accordance with claim 2, wherein said non-magnetic material is selected from the group consisting of a plastic, wood, rubber and mixtures thereof.

4. The hammer-like tool in accordance with claim 1, which has a handle made of a material selected from the group consisting of a metal, plastic, wood and mixtures thereof.

5. A hammer-like therapeutic tool for striking a the body of a user, comprising:
   a handle;
   a head, attached to the handle, having a face for striking the body;
   an antenna mounted on the head adjacent to the face;
   a radio-frequency oscillator, means disposed within the tool and coupled to the antenna, for driving the antenna to emit radio waves in the frequency range of about 100 KHz to 10 MHz; and
   means, disposed within the tool, for supplying voltage pulses to the oscillator upon impact of the face on the body such that radio waves are emitted upon impact.

6. The tool according to claim 5, wherein the means for supplying voltages pulses includes an induction coil mounted within the head and a magnet freely movable into and out of the induction coil upon motion of the head, whereby motion of the head may move the magnet through the induction coil to induce a voltage pulse for powering the oscillator.

7. The tool according to claim 5, wherein the antenna includes a radiating coil including an open coil end adjacent the face.

* * * * *